United States Patent
Earhart et al.

(10) Patent No.: US 12,161,319 B2
(45) Date of Patent: Dec. 10, 2024

(54) INSTRUMENT FOR MANUAL INSERTION OF A BUTTON

(71) Applicant: Arthrex, Inc., Naples, FL (US)

(72) Inventors: Todd Earhart, Naples, FL (US); Pete Denove, Naples, FL (US); Karen Gallen, Naples, FL (US); Darren Thomsen, Naples, FL (US)

(73) Assignee: Arthrex, Inc., Naples, FL (US)

( * ) Notice: Subject to any disclaimer, the term of this patent is extended or adjusted under 35 U.S.C. 154(b) by 18 days.

(21) Appl. No.: 18/180,941

(22) Filed: Mar. 9, 2023

(65) Prior Publication Data
US 2023/0218290 A1   Jul. 13, 2023

Related U.S. Application Data

(63) Continuation of application No. 15/278,804, filed on Sep. 28, 2016, now abandoned.

(51) Int. Cl.
*A61B 17/04* (2006.01)

(52) U.S. Cl.
CPC .. *A61B 17/0401* (2013.01); *A61B 2017/0404* (2013.01); *A61B 2017/0409* (2013.01); *A61B 2017/0414* (2013.01)

(58) Field of Classification Search
CPC ............ A61B 17/0401; A61B 17/0642; A61B 2017/0404; A61B 2017/0406; A61B 2017/0408; A61B 2017/0409; A61B 2017/0411; A61B 2017/0414
See application file for complete search history.

(56) References Cited

U.S. PATENT DOCUMENTS

| | | | | |
|---|---|---|---|---|
| 5,041,129 A | * | 8/1991 | Hayhurst | A61B 17/0401 606/220 |
| 5,948,002 A | * | 9/1999 | Bonutti | A61B 17/3468 606/232 |
| 8,348,960 B2 | | 1/2013 | Michel | |
| 9,357,989 B2 | | 6/2016 | Tallarida | |
| 9,918,711 B2 | | 3/2018 | Seavey | |
| 2005/0033363 A1 | | 2/2005 | Bojarski | |
| 2007/0162125 A1 | | 7/2007 | LeBeau | |
| 2008/0140093 A1 | | 6/2008 | Stone | |

(Continued)

FOREIGN PATENT DOCUMENTS

| | | |
|---|---|---|
| EP | 2014241 A2 | 1/2009 |
| EP | 2599449 A1 | 6/2013 |

OTHER PUBLICATIONS

International Preliminary Report on Patentability for PCT application No. PCT/US2017/051708, mailed Apr. 11, 2019.

(Continued)

*Primary Examiner* — Martin T Ton
(74) *Attorney, Agent, or Firm* — McDonnell Boehnen Hulbert & Berghoff LLP

(57) ABSTRACT

A button inserter includes a shaft having a fulcrum that extends beyond a distal tip of the shaft. An inner rod is within the shaft and has a button mating surface that extends from a distal tip of the inner rod. A handle includes a handle switch that translates the inner rod between an extended position where the button mating surface of the inner rod extends beyond the distal tip of the shaft and a retracted position where the button mating surface of the inner rod is located completely within the shaft.

16 Claims, 3 Drawing Sheets

(56) References Cited

U.S. PATENT DOCUMENTS

| | | | |
|---|---|---|---|
| 2009/0043318 A1* | 2/2009 | Michel | A61B 17/0401 606/232 |
| 2009/0105754 A1 | 4/2009 | Sethi | |
| 2011/0172682 A1 | 7/2011 | Brady | |
| 2012/0203249 A1* | 8/2012 | Schmidt | A61F 2/0811 606/144 |
| 2013/0138108 A1 | 5/2013 | Dreyfuss | |
| 2015/0051621 A1 | 2/2015 | Sorensen | |

OTHER PUBLICATIONS

International Search Report and Written Opinion for PCT application No. PCT/US2017/051708, mailed Nov. 27, 2017.

\* cited by examiner

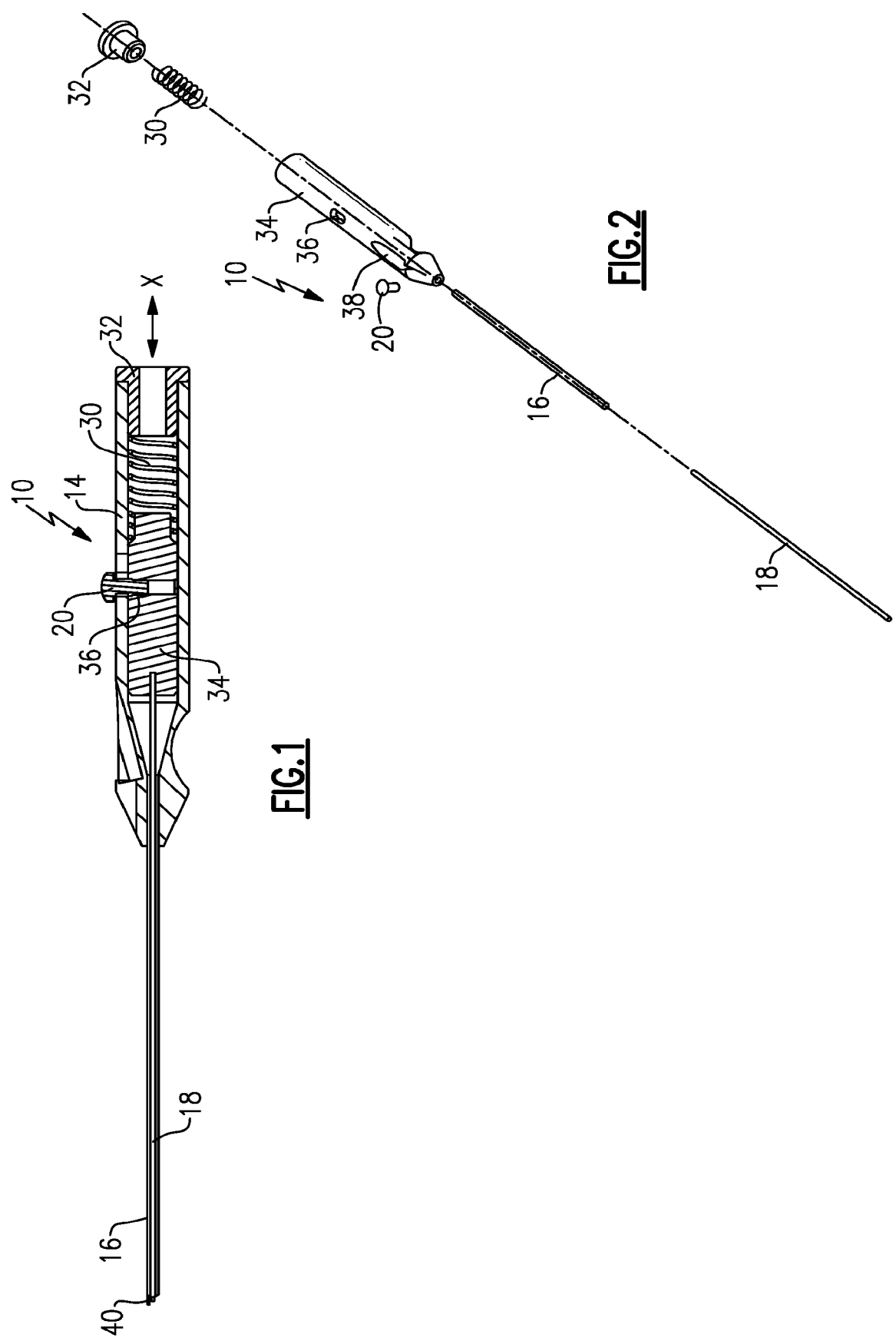

INSTRUMENT FOR MANUAL INSERTION OF A BUTTON

CROSS-REFERENCE TO RELATED APPLICATION

This application is a continuation of U.S. patent application Ser. No. 15/278,804, filed Sep. 28, 2016, the entire contents of each of which are incorporated herein by reference in its entirety for all purposes.

BACKGROUND

A button inserter is employed to pass a button construct through a drilled bone tunnel for positioning and deployment of the button on the cortex of a bone. Typically, pull-through sutures and needle are required to advance a suture button through a bone tunnel and for deployment of the button onto the distal cortical surface of the bone. The use of pull-through sutures and needle requires the perforation of the periosteum and soft-tissue adjacent to the exit plane of the bone tunnel, commonly referred to as an "inside-out" technique. The use of pull-through sutures and needle associated with an "inside-out" technique can cause a surgeon to advance the suture button farther than necessary to deploy and flip the button into its position on the bone cortex. Advancing the device farther than necessary may also cause soft-tissue to become trapped underneath the button when seated on the bone cortex resulting in the button being positioned proud on the bone surface.

SUMMARY

A button inserter includes a shaft and an inner rod within the shaft. The inner rod has a button mating surface that extends from a distal tip of the inner rod and engages a button. A handle includes a handle switch that translates the inner rod between a first position and a second position. The button inserter is used to position the button beyond a bone, and the inner shaft translates from the first position to the second position to release the button from the end of the button inserter, allowing the button to flip.

In an embodiment, a button inserter includes a shaft having a fulcrum that extends beyond a distal tip of the shaft. An inner rod is within the shaft and has a button mating surface that extends from a distal tip of the inner rod. A handle includes a handle switch that translates the inner rod between an extended position where the button mating surface of the inner rod extends beyond and communicates with the distal button mating surface of the shaft and a retracted position where the button mating surface of the inner rod is located completely within the shaft.

In another embodiment, the handle includes a resilient member and a slide both located inside the handle. The resilient member moves the slide away from a distal end of the handle to retract the inner rod when the handle switch is released.

In another embodiment, a surgical system includes a button inserter. The button inserter includes a shaft including a fulcrum that extends from a distal tip of the shaft and an inner rod within the shaft that has a button mating surface that extends from a distal tip of the inner rod. The button inserter includes a handle including a handle switch that translates the inner rod between an extended position where the button mating surface of the inner rod extends beyond the distal end of the shaft and a retracted position where the button mating surface of the inner rod is completely within the shaft. An oblong button includes a congruent mating surface to the button mating surface of the inner rod of the button inserter. When the oblong button is attached to the inserter in the extended position, the oblong button is constrained rotationally and translationally by the fulcrum of the shaft and the button matting surface on the inner rod of the inserter. A suture strand passes through an opening of the oblong button.

In another embodiment, the surgical system includes a second button.

In another embodiment, the handle includes a groove and a pair of resilient arms, and the second button is located in the groove and secured to the handle by the pair of resilient arms.

In another embodiment, the oblong button is substantially parallel to a longitudinal axis of the shaft in the initial position, and the second button is substantially perpendicular to the longitudinal axis of the shaft in a deployed position.

In another embodiment, the second button is a round button.

In another embodiment, the suture strand passes through an opening of the second button.

In another embodiment, the suture strand imparts an off-axis tensile force between the oblong button and the second button.

In another embodiment, a surgical method includes the steps of inserting an oblong button into a bone tunnel. The oblong button is mated to a button inserter. The button inserter includes a shaft including a fulcrum that extends from a distal tip of the shaft, an inner rod within the shaft having a button mating surface extending from a distal tip of the inner rod, and a handle including a handle switch. The handle switch translates the inner rod between an extended position where the button mating surface of the inner rod extends beyond the distal end of the shaft and a retracted position where the button mating surface of the inner rod is completely within the shaft. The method includes the steps of releasing the handle switch and retracting the button matting surface into the shaft of the button inserter to allow rotational motion about a transverse axis of the oblong button. In an embodiment, the oblong button is secured against the bone surface, and the inserter is withdrawn through the bone tunnel.

In an embodiment according, a bone tunnel can be in any short, long, or irregular bone. In another embodiment, the bone tunnel is through a tibia, fibula, or both tibia and fibula. For example, a system as disclosed herein can be used for ankle syndesmosis with or without associated ankle fracture repair.

In another embodiment, the oblong button rests against a medial cortex of a bone.

In another embodiment, the bone is a tibia.

In another embodiment, a second button is positioned against a lateral side of a bone.

In another embodiment, the second button is positioned against a lateral side of a second bone.

In another embodiment, a second button is positioned against a bone plate.

In another embodiment, the second button is a round button. In another embodiment according, the second button is a dog bone shaped button.

These and other features of the present invention can be best understood from the following specification and drawings, the following of which is a brief description

BRIEF DESCRIPTION OF THE DRAWINGS

FIG. 1 illustrates a side cross-sectional view of a button inserter used to insert a distal button through a drilled passage in a bone;

FIG. 2 illustrates an expanded view of the button inserter;

DETAILED DESCRIPTION

Figure 3:
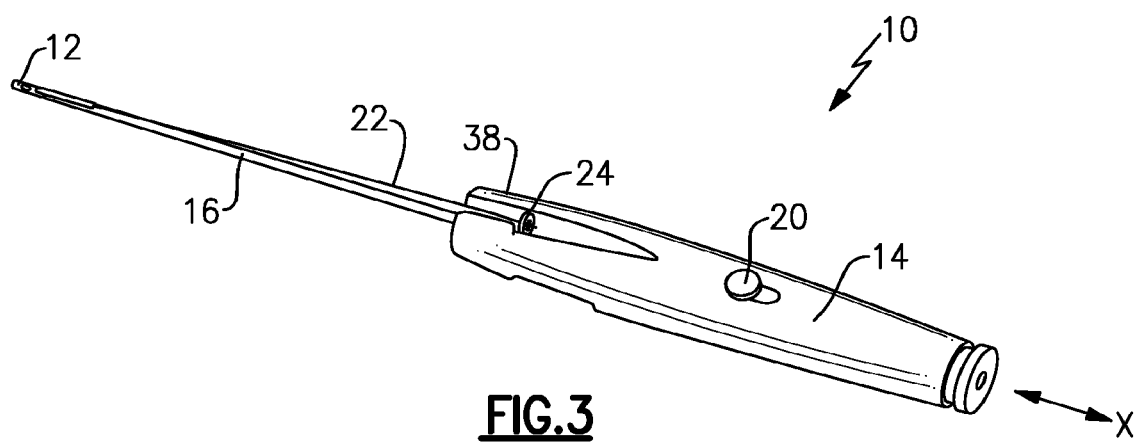
FIG. 3 illustrates a perspective view of the button inserter.

FIGS. 1 to 3 illustrate a suture button inserter 10 used to manually insert an oblong button 12 through a drilled bone tunnel. The suture button inserter 10 includes a handle 14, a shaft 16, and an inner rod 18 located inside the shaft 16. The inner rod 18 includes a button mating surface, which extends beyond the distal tip of the shaft 16. When the inner rod 18 is deployed, the inner rod 18 can translate relative to the shaft 16 to position the button mating surface inside the shaft 16. The handle 14 includes a handle switch 20 and a suture strand 22 that is secured and wrapped around the handle switch 20. When the handle switch 20 is released, a resilient member 30 (for example, a spring) located between a cap 32 (located at a proximal end of the handle 14) and a slide 34 (located inside the handle 14) moves the slide 34 away from a distal end of the handle 14. The slide 34 translates the inner rod 18 through the shaft 16 from the extended position to a retracted position. In one example, a proximal end of the inner rod 18 is received in an opening in the slide 34. When in the extended position, the handle switch 20 is received in an opening 36 in the slide 34 to prevent movement of the slide 34 and therefore the inner rod 18.

Figure 4:
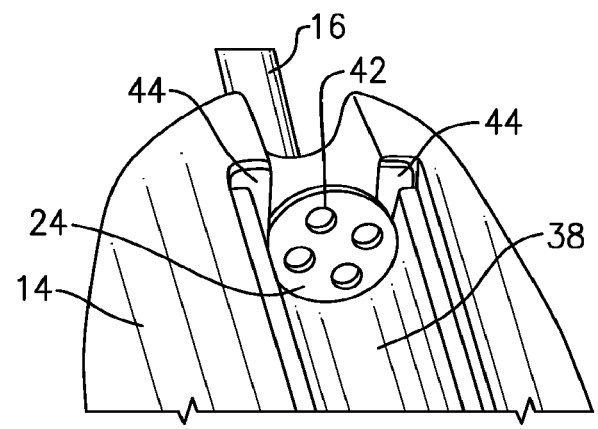
FIG. 4 illustrates a top view of a round button in a handle of the instrument.

As shown in FIG. 4, the handle 14 includes a groove 38, and a round button 24 is located within the groove 38. A pair of resilient arms 44 retain the round button 24 to the handle 14. The round button 24 is substantially perpendicular to a longitudinal axis X of the shaft 16. In one example, the round button 24 may be other shapes (e.g., dog bone or oblong).

Figure 5:
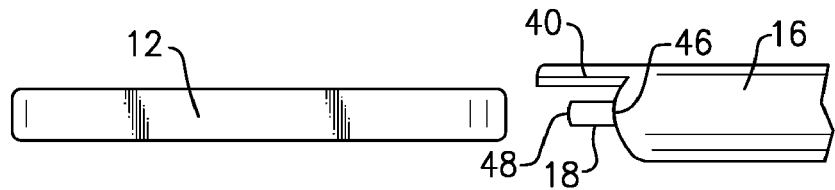
FIG. 5 illustrates a side view of a shaft including an inner rod that engages the oblong button.
Figure 6:
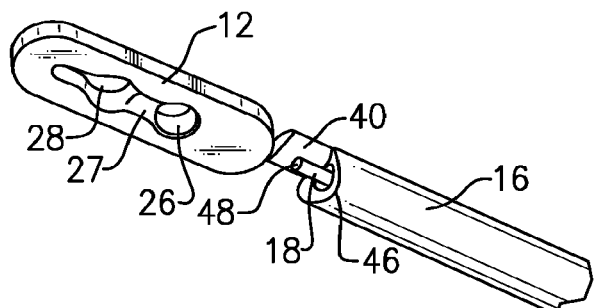
FIG. 6 illustrates a perspective exploded view of the shaft, the inner rod, and the oblong button.
Figure 7:
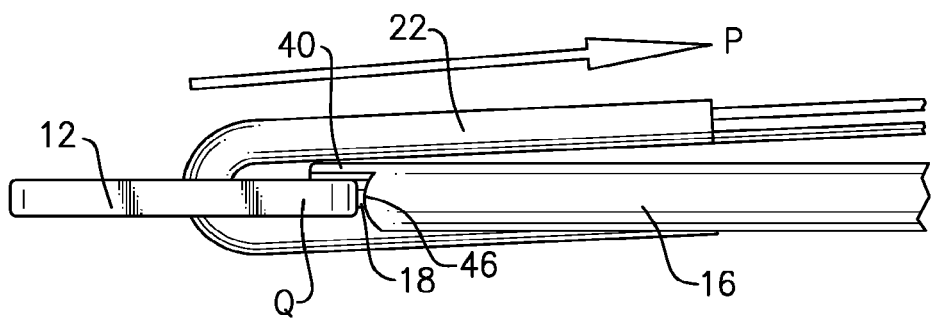
FIG. 7 illustrates a fulcrum of the button inserter at a distal end of the shaft.

As shown in FIGS. 5 to 6, a distal end of the shaft 16 includes a fulcrum 40 that extends beyond a distal tip 46 of the shaft 16. In the extended position, the button mating surface of the inner rod 18 extends beyond the distal tip 46 of the shaft 16. When the oblong button 12 is attached to the button inserter 10 in the extended position, the oblong button 12 is constrained rotationally and translationally by the fulcrum 40 of the shaft 16 and the button matting surface on the inner rod 18 of the button inserter 10. The inner rod 18 has a button mating surface that extends from a distal tip 48 of the inner rod 18. The button mating surface of the inner rod 18 engages a congruent mating surface of the oblong button 12.

When the inner rod 18 moves to the retracted position, the button mating surface of the inner rod 18 is located completely within the shaft 16. The oblong button 12 flips to a deployed position about the fulcrum 40 of the shaft 16. In one example, the deployed position is substantially perpendicular to the initial position.

In one example, the inner rod 18 is received in an opening (not shown) of the oblong button 12 and retains the oblong button 12 to the button inserter 10. In one example, the oblong button 12 is substantially parallel to the longitudinal axis X of the shaft 16 when in an initial position. In the initial position, the oblong button 12 is rotationally and translationally constrained. The oblong button 12 includes a proximal opening 26, a distal opening 28, and a channel 27 that is located between the proximal opening 26 and the distal opening 28. The suture strand 22 passes through the proximal opening 26 of the oblong button 12. The suture strand 22 also extends through an opening 42 in the round button 24 and is wrapped around the handle switch 20. The oblong button 12 and the round button 24 can be made of stainless steel, titanium alloy, titanium, PEEK or PLLA, or any other material.

When the inner rod 18 translates relative to the shaft 16 to the retracted position, the suture strand 22 applies an off-axis tensile force P between the oblong button 12 and the round button 24. Without the button mating surface constraining movement, the oblong button 12 rotates to the deployed position about the transverse axis Q at an interface between the oblong button 12 and the fulcrum 40. The off-axis is non-parallel to the longitudinal axis.

A bone tunnel is drilled in at least one bone. In one example, a bone tunnel is drilled in a tibia, in a fibula, or in both the tibia and the fibula.

In an example, the shaft 16 of the button inserter 10 is inserted into and through a bone tunnel in a first bone and a second bone. The oblong button 12 is mated to the button inserter 10. Once the oblong button 12 (which is in the initial position) is located beyond the both bones, the handle switch 20 of the handle 14 is released. The button matting surface of the inner rod 18 retracts into the shaft 16 of the button inserter 10. Due to the off-axis force P applied by the suture strand 22, the oblong button 12 will rotate, or flip, about the transverse axis Q to the deployed position. In the deployed position, the oblong button 12 is substantially perpendicular to the axis X of the instrument 10. In use, the shaft 16 prevents the oblong button 12 from traveling back through the bone tunnel. The round button 24 is released from the handle 14. The suture strand 22 extends between the first bone and the second bone to provide fixation.

In one example, the oblong button 12 rests against a medial cortex of a bone. The second button 24 can be positioned against a lateral side of the bone. In another example, the oblong button 12 is positioned against the first bone, and the second button 24 is positioned against a lateral side of the second bone. The oblong button 12 can be positioned against the medial cortex of the first bone. In yet another example, the round button 24 is positioned against a bone plate. Although the fixation of bone to bone has been described, the button inserter 10 can also be used for the fixation of soft tissue to bone.

The button inserter 10 allows the oblong button 12 to be pushed into position through a bone tunnel instead of being pulled through the bone tunnel with a suture and a needle. This allows for easier deployment of buttons. The oblong button 12 also prevents lateral tissue entrapment.

In an embodiment, the suture strand can be a flexible material, e.g., suture or suture tape. In another embodiment, the suture strand can be an adjustable or non-adjustable loop. In an embodiment, the combination of the suture strand and buttons in the disclosed systems can be an adjustable, knotless button/loop construct. In an embodiment, a knotless loop construct is self-locking.

A button inserter and a surgical system as disclosed herein can also be used in procedures for ankle syndesmosis repair and for fracture management (e.g., ankle, wrist, hand, etc.).

For example, a method of ankle syndesmosis repair (with or without ankle fracture) includes a) inserting an oblong button into bone tunnels traversing the tibia and fibula, wherein the oblong button is mated to a button inserter as disclosed herein; b) releasing the handle switch, whereby the button mating surface retracts into the shaft of the button inserter to allow rotational motion of the button; and c) securing the oblong button on the medial tibial cortex. The method can further include withdrawing the button inserter through the tibial and fibular bone tunnels. The method can also include adjusting a suture strand so there is no excess flexible material. The method can also include securing a second button against a bone plate on the lateral surface of the fibula. In an embodiment, the second button can be secured by tightening the suture strand (e.g., cinching an adjustable construct). In an embodiment, the second button is a round button.

In an embodiment, a method includes reducing a fracture prior to preparing bone tunnels. In an embodiment, reducing the fracture includes mounting a bone plate to the fractured bone(s). In an embodiment, a method includes reducing a fracture of the fibula prior to preparing bone tunnels through the fibula and/or tibia. In an embodiment of ankle syndesmosis repair, a method includes attaching a bone plate to a fibula prior to repairing a bone tunnel.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A surgical system comprising:
   a) a button inserter comprising:
      i) a shaft including a projection that defines a fulcrum at a distal end of the projection, wherein the projection extends beyond a distal tip of the shaft;
      ii) an inner rod within the shaft having a button mating surface extending from a distal tip of the inner rod; and
      iii) a handle including a handle switch that translates the inner rod between an extended position where the button mating surface of the inner rod extends beyond the distal tip of the shaft and a retracted position where the button mating surface of the inner rod is completely within the shaft;
   b) an oblong button including a congruent mating surface to the button mating surface of the inner rod of the button inserter, wherein the oblong button is constrained rotationally and translationally by (i) the projection of the shaft that defines the fulcrum and (ii) the button mating surface on the inner rod of the inserter when the inner rod of the button inserter is in the extended position;
   c) a second button configured to be removably coupled to the handle; and
   d) a suture strand passing through an opening of the oblong button passing over the projection and further passing through an opening of the second button, wherein when the inner rod translates relative to the shaft to the retracted position, the suture strand applies an off-axis force to rotate the oblong button about the fulcrum from an initial position to a deployed position.

2. The surgical system of claim 1, wherein the handle includes a groove and a pair of resilient arms, and the second button is located in the groove and removably coupled to the handle by the pair of resilient arms.

3. The surgical system of claim 1, wherein the oblong button is substantially parallel to a longitudinal axis of the shaft in the initial position and the oblong button is substantially perpendicular to the longitudinal axis of the shaft in the deployed position.

4. The surgical system of claim 1, wherein the suture strand imparts an off-axis tensile force between the oblong button and the second button.

5. The surgical system of claim 1, wherein the projection is an integral, unitary, monolithic part of the shaft.

6. The surgical system of claim 1, wherein the button mating surface contacts the congruent mating surface of the oblong button in the initial position to thereby constrain translational and rotational motion of the oblong button, and wherein the button mating surface does not contact the oblong button in the deployed position.

7. The surgical system of claim 1, wherein the suture strand is coupled to the handle switch.

8. The surgical system of claim 1, wherein the opening of the oblong button comprises a proximal opening, and wherein the oblong button further comprises a distal opening.

9. The surgical system of claim 8, wherein the oblong button further comprises a channel positioned between the proximal opening and the distal opening.

10. The surgical system of claim 8, wherein the suture strand is positioned only in the proximal opening.

11. The surgical system of claim 1, wherein the off-axis is non-parallel to a longitudinal axis of the shaft.

12. The surgical system of claim 1, wherein the second button is a round button.

13. The surgical system of claim 1, wherein the second button is oblong or a dog bone shape.

14. The surgical system of claim 1, wherein the second button is substantially perpendicular to a longitudinal axis of the shaft when the second button is removably coupled to the handle.

15. The surgical system of claim 1, further comprising:
   a cap positioned at a proximal end of the handle;
   a slide positioned inside of the handle and coupled to the inner rod; and
   a resilient member positioned between the cap and the slide,
   wherein the resilient member is configured to move the slide away from a distal end of the handle to thereby translate the inner rod through the shaft from the extended position to the retracted position.

16. The surgical system of claim 15, wherein the handle switch is positioned in an opening in the slide when the inner rod is in the extended position to thereby prevent movement of the slide and the inner rod.

* * * * *